United States Patent
Fleischer

(10) Patent No.: US 7,563,416 B2
(45) Date of Patent: Jul. 21, 2009

(54) SAFETY DEVICE FOR AIR IN AT LEAST ONE ROOM OF A BUILDING

(75) Inventor: Werner Fleischer, Schwarzenberg (CH)

(73) Assignee: LK Luftqualität AG, Littau (CH)

( * ) Notice: Subject to any disclaimer, the term of this patent is extended or adjusted under 35 U.S.C. 154(b) by 863 days.

(21) Appl. No.: 10/493,475

(22) PCT Filed: Oct. 24, 2002

(86) PCT No.: PCT/IB02/04952

§ 371 (c)(1),
(2), (4) Date: Apr. 23, 2004

(87) PCT Pub. No.: WO03/036181

PCT Pub. Date: May 1, 2003

(65) Prior Publication Data

US 2004/0258585 A1  Dec. 23, 2004

(30) Foreign Application Priority Data

Oct. 26, 2001  (DE) ................................ 101 53 575

(51) Int. Cl.
*B01J 19/08* (2006.01)
(52) U.S. Cl. ............................ 422/186.04; 422/186.07; 422/121; 361/231
(58) Field of Classification Search .................. 422/121, 422/22, 186, 186.07; 204/164; 96/417, 18; 361/231
See application file for complete search history.

(56) References Cited

U.S. PATENT DOCUMENTS

| | | | | |
|---|---|---|---|---|
| 5,354,994 A | * | 10/1994 | Hicks | 250/559.36 |
| 5,613,271 A | * | 3/1997 | Thomas | 15/321 |
| 5,657,664 A | * | 8/1997 | Birchmeier | 74/89.19 |
| 5,695,396 A | * | 12/1997 | Markwart et al. | 454/76 |
| 5,827,407 A | * | 10/1998 | Wang et al. | 204/164 |
| 6,716,406 B2 | * | 4/2004 | Reisfeld et al. | 423/245.1 |

* cited by examiner

Primary Examiner—Alexa D Neckel
Assistant Examiner—Xiuyu Tai
(74) Attorney, Agent, or Firm—Gudrun E. Huckett

(57) ABSTRACT

A safety device for the air in a room has an intake air channel for supplying outside air to the room. A device for air treatment is provided. A detector for air contaminants is arranged in the intake air channel. A safety closure with a drive is arranged in the air intake channel and has an open position and a closed position for airtightly closing the intake air channel or an inlet of the device for air treatment that is arranged downstream of the safety closure. An exhaust air channel is connected to the room and the device for air treatment. When the safety closure is in the open position, a partial recirculating operation occurs. When the safety closure is in the closed position, a complete recirculating operation is present. The device for air treatment, the detector, and the drive are connected to a control device.

9 Claims, 2 Drawing Sheets

SAFETY DEVICE FOR AIR IN AT LEAST ONE ROOM OF A BUILDING

BACKGROUND OF THE INVENTION

The invention relates to safety devices for the air in at least one room of a building, wherein the room has at least one supply air channel for taking in outside air and at least one device for air treatment.

Known devices for air treatment in the form of, for example, air-conditioning devices for buildings, have the disadvantage that they do not protect human beings from occurring air contaminants, in particular, hazardous substances or organisms.

SUMMARY OF THE INVENTION

The invention concerns the problem of protecting human beings in rooms against occurring air contaminants, in particular, hazardous substances or organisms.

This problem is solved in that in the intake air channel at least one detector for air contaminants is arranged that converts at least one input signal into an output signal representing the value of one or several parameters, in that a safety closure coupled to a drive is arranged such that this safety closure does not close at least partially or closes airtightly the intake air channel or the entrance of the device for air treatment, in that the device for air treatment is arranaed in the flow direction of the outside air downstream of the safety closure, in that the room is provided with at least one exhaust air channel, in that the exhaust air channel is connected to the device for air treatment such that for the safety closure in the open position a partial recirculating operation or for the safety closure in the closed position a complete recirculating operation is present, and in that the device for air treatment, the detector for air contaminants, and the drive are connected to at least one control device.

The safety device for the air in at least one room of a building, wherein the room has at least one supply air channel for taking in outside air and at least one device for air treatment, is characterized in particular in that the human beings in the room are protected against air contaminants, in particular, in the form of hazardous substances or organisms. This is achieved in that within the supply air channel at least one detector for air contaminants is arranged and is connected by means of a control device to a safety closure that airtightly closes off the supply air channel when air contaminants occur. Advantageously, the detector is arranged at the beginning of the supply air channel while the safety closure is arranged at its end. At the end of the supply air channel, a device for air treatment is provided. Air treatment of the room air results in that a portion of the exhaust air of the room is treated such that it can be used as intake air for the room. With such devices for air treatment the outside air proportion can be less than 10%. In the case of a hazardous situation, a decoupling from the outside air for an extended period of time is possible only with such a device. A special advantage results in that also several rooms can be decoupled from the outside air when air contaminants occur. With the device or devices for air treatment, this state can also be maintained over an extended period of time. In this period of time, further measures can be carried out for hazard control. The special advantage of the safety device according to the invention resides in that automatically the room is sealed off and in that the exhaust air of the room or of the rooms is treated again.

When no danger sources are present, a proportion of the outside air is treated together with the exhaust air of the room as recirculating air. This proportion of the required outside air can be up to a value of less than 10%. In normal operation with supply of outside air, a proportion of the exhaust air is not treated anew as recirculating air but reaches the environment as escape air. This escape channel is closed off when the safety device is in operation.

The safety device according to the invention is characterized furthermore in that during operation there is substantially no vacuum produced; instead, over an extended period of time, a pressure compensation takes place.

Beneficial detectors are a sensor for at least one chemical substance, a sensor for a biological organism, a dosemeter, or a device for determining air-borne particles. In particular, a combination of all these detectors provides an optimal protection form air contaminants. In this connection, chemical substances, biological organisms, energy-rich radiation, particles contaminated with energy-rich radiation, or contaminant-laden air-borne particles can be detected.

When at least one of these substances, organisms, or particles is detected, the safety closure provided in or on the supply air channel is actuated so that the room is sealed airtightly. Of course, additional sensors or devices for determining health-hazardous substances or organisms can be provided also as a detector for air contaminants.

By means of a known luminescence dosemeter, the radiation acting on the luminescence dosemeter can be optically determined. A special advantage resides in that for such a luminescence dosemeter the received radiation is continuously added wherein, upon reading of the received radiation, the equivalent luminescence is not lost. The luminescence is not quenched during reading. When several luminescence dosemeters are used, a continuous control can be ensured. During reading of a first luminescence dosemeter, the second luminescence dosemeter also records the radiation during reading of the first luminescence dosemeter.

The first airflow sensor in the supply air channel is used for measuring the airflow in the supply air channel. Based on this, it can be determined whether:
 the safety closure in the reaction time in the form of the switching times as delay times and the inertia of the safety closure has been closed and/or
 the safety as a function of the airflow is ensured or measures for lowering airflow are required.

Positioning of the detector for air contaminants in the end area of the intake opening of the supply air channel advantageously results in that across the length of the supply air channel the switching times as delay times and the inertia of the safety closure up to the point of airtight sealing can be bridged such that the air contaminants up to an airtight closure will not escape from the supply air channel and therefore surely cannot reach the room. According to another embodiment, the volume of the supply air channel is configured according to the airflow velocity in the supply air channel and/or as a function of the time delays of the detectors for air contaminants, the control device, and the drive including the inertia of the safety closure.

The Another embodiment advantageously provides air treatment of the room by ionization. Ionization is based on electrical discharge in ionization tubes or on corona discharges. The level of the ionization power is determined based on values of oxidizable air components (for example, vaporous organic compounds—VOC), the relative humidity, and the flow velocity/volume flow of the air to be treated and detected by a first air quality sensor, an airflow sensor, and an air humidity sensor and/or a second air quality sensor, while ensuring a minimum intensity of positive and negative oxygen ions (adequate to the air state in nature). The device for air treatment is controlled such that particularly the load of the outside air with volatile hydrocarbons is measured with a first air quality sensor, the flow velocity or the volume flow of the air to be treated with an air flow sensor, the relative humidity of the air to be treated with an air humidity sensor, and the oxidizable air components of the exhaust air and/or recirculating air by means of a second air quality sensor in the recirculating air channel between the room and the air treatment device and, based on the values of the measurements, the level of the ionization power of at least one or several ionization apparatus is controlled such that a minimum intensity of oxygen ions is ensured.

In this way, the proportion of outside air can be significantly reduced.

A further embodiment leads advantageously to an air treatment of the room by ionization by taking into consideration the ozone contents. The ionization is based on electrical discharge in ionization tubes or corona discharges. The level of ionization power is determined based on values of oxidizable air components (for example, vaporous organic compounds—VOC), the relative humidity, and the flow velocity/volume flow and the ozone load of the air to be treated detected by a first air quality sensor, an airflow sensor, an air humidity sensor, an ozone sensor, and/or a second air quality sensor, while ensuring a minimum intensity of positive and negative oxygen ions (adequate to the air state in nature). The device for air treatment is controlled such that in particular the load of the outside air with volatile hydrocarbons is measured by means of a first air quality sensor, the flow velocity or the volume flow of the air to be treated by means of an airflow sensor, the relative air humidity in the air to be treated by means of an air humidity sensor, the contents of ozone in the intake air by means of an ozone sensor, and the oxidizable air components of the exhaust air and/or of the recirculating air by means of a second air quality sensor within the recirculating air channel between the room and the air treatment device, and, based on the values of the measurements, the level of ionization power of at least one or several ionization apparatus is controlled such that the minimum intensity of the oxygen ions, when an ozone value that is too high occurs, the ozone is reduced by forming free radicals as well as naturally occurring oxygen clusters.

The special advantage resides in that in particular the value of the ozone in the intake air is also evaluated and controlled accordingly, and, when reaching/surpassing preset points, signals are sent to the control device. In this way, the ionization apparatus is controlled such that a damaging effect on persons within the room is substantially avoided. This is based on the ozone sensor in the supply air channel of the room that is connected by means of the control device to the ionization apparatus. For an actual stable intake air ionization that is adequate to nature, wherein a preset ozone limit value is not surpassed and in an extreme situations ozone is eliminated, the control device supplies optimized alternating pulses that are sent to the at least one ionization apparatus. Each alternating pulse is a complete sine curve which is cut at the zero crossing. The frequency is not changed in this connection. Advantageously, several alternating pulses (several sine curves) are combined to packages or sets. The package size and thus the number of alternating pulses per package or set provides a possibility for optimizing the air ionization and for minimizing at the same time the load on the electrical mains. The discharge voltage remains constant in this connection so that a stable air ionization is ensured. In this way, the proportion of outside air can be substantially lowered.

By means of a temporally supplied periodic alternating voltage a favorable control of the ionization apparatus is provided. In this connection, the ionization apparatus is supplied with alternating pulses or alternating pulses combined to packages of a periodic alternating voltage that is available. The optimized discharge voltage is constant in this connection.

The proportion of ozone is lowered such that the desired and predetermined limit values are ensured. In a first range, the power of the ionization apparatus is lowered. When the value of the ozone contents of the intake air increases despite lowering of air ionization, at least one external ozone source is present. In this case, automatically a mode for decomposing ozone is switched on by the control device. When the preset limits are reached again, the device for air treatment is returned to normal operation. In this connection, the energy level of the ozone is changed such that it decomposes. The preset values for signalizing certain ozone values are selected such that sufficient reaction safety is present.

This spring return drive as a drive for the safety closure ensures an open safety closure when the spring return drive is not triggered. This configuration ensures an economic realization with minimal energy costs.

By means of the escape air channel a portion of the room air reaches the environment. The exhaust air that in this way escapes the room and the device for air treatment is replaced by outside air through the supply air channel.

At least one additional ozone sensor in the supply air channel and/or in the recirculating air channel advantageously ensures that ozone generated in at least one room is measured immediately. Switching delays do not cause ozone to be fed into the room. The ozone that is formed within the room originates in particular from external sources in the room, for example, printers or copiers. Another advantage results when placing an ozone sensor in the supply air channel, wherein ozone that is taken in from the exterior is detected. This ozone originates also from external sources, for example, motor vehicles or other devices that cause air contamination. The special advantage resides in that this ozone is decomposed. This is particularly important in connection with a closed room. Of course, ozone generated in other ways is also decomposed in the intake air.

The ozone decomposition is carried out in the pauses between the alternating pulses, the alternating pulse rates and/or the packages of alternating pulses by means of the compensation of charges of the ionized air that is taking place in this connection, wherein the ozone is converted into natural oxygen clusters/charged oxygen molecules. This is taken into consideration wherein in that these pauses are generated in a targeted fashion by the control device, and, in this way, the decomposition of the ozone is carried out.

With the at least one manually actuatable switch, wherein the safety closure is closed after actuation, the safety closure, independent of monitoring by the detector for air contamination in the supply air channel, can be closed based on a warning message. In this way, the feeling of being safe can be significantly increased for persons within the room.

BRIEF DESCRIPTION OF THE DRAWINGS

One embodiment of the invention is illustrated in the drawings and will be explained in the following in more detail.

It is shown in.

DESCRIPTION OF PREFERRED EMBODIMENTS

Figure 1:
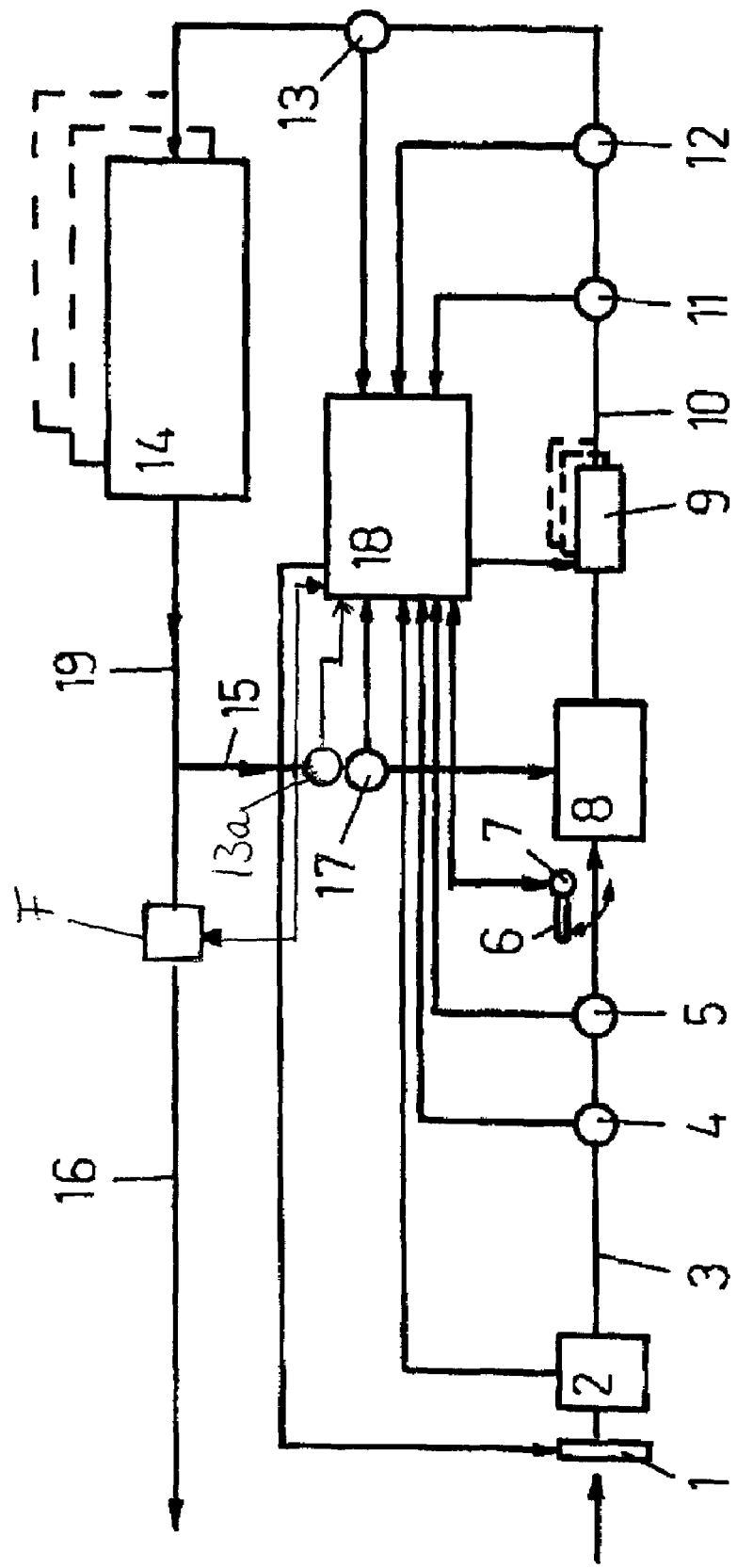
FIG. 1 a schematic view of the safety device for the air in at least one room of a building.

A safety device for the air in at least one room 14 of a building is comprised of an intake air channel 3 for taking in outside air, a device for air treatment, a safety closure in the form of a safety flap 6 coupled to a drive, an exhaust air channel 19, and at least one detector for air contaminants 2 (illustration in FIG. 1). Of course, other mechanisms that ensure an open state as well as a closed state can be used as safety closures.

In the end area of the opening of the intake air channel 3 the detector for air contaminants 2 is provided. It converts at least one input signal into an output signal that represents the value of one or several parameters. This is, in particular, a sensor for at least one chemical substance, a sensor for a biological organism, a dosemeter, or a device for determining air-borne particles; they are used individually or in at least one combination. The sensor for at least one chemical substance changes its electrical or optical properties or puts out an electrical signal when a chemical substance is present. The sensor for at least one biological organism operates according to the same principle. The biological organism in this connection is, for example, a bacterium or a virus. The dosemeter is a luminescence dosemeter. In this connection, luminescence refers to the emission of photons in the visible spectral range in solid bodies during or after action on the crystal wherein energy is transmitted in some form onto the crystal. This can be realized by radiation of visible light or UV radiation, by particle exposure or excitation by other ionizing radiation and by chemical, mechanical, or thermal effects on the crystal. In the device for determining air-borne particles, particularly the geometry of the particles is determined. Based on the geometry, it is possible to deduce the type of particle, wherein the shape, the contour, the surface area of the contour, but also the color, the luminescence and/or phosphorescence can be classified and, based on this classification, the type and its properties/hazard can be determined.

The volume of the intake air channel 3 is configured in accordance with the airflow velocity in the intake air channel 3 and/or as a function of the time delays of the detector for air contaminants 2, the control device 18, and the drive 7 including the inertia of the safety flap 6.

Downstream of the intake air channel 3, the safety flap 6 that is coupled to the drive 7 is present that interrupts the airflow from the exterior in an airtight way when triggered. The room 14 is provided with at least one exhaust air channel 19. The exhaust air channel 19 is connected to the device for air treatment such that, when the safety flap 6 is open, a partial recirculating operation or, when the safety flap 6 is closed, a complete recirculating operation is present. The drive 7 for the safety flap 6 is, for example, a spring return drive. The drive 7 can also be formed according to another embodiment as a magnet drive. Moreover, in further embodiments sensors for indicating the states of open or closed components of the safety device can be present. In the intake air channel 3 a first airflow sensor 4 is arranged.

The device for air treatment is arranged in the flow direction of the outside air downstream of the safety flap 6 and is comprised of an air treatment device 8, a first air quality sensor 5, a second air quality sensor 17, an ionization apparatus 9, a second airflow sensor 11, an air humidity sensor 12, and an ozone sensor 13. The air quality sensors 5, 17, the airflow sensors 4, 11, the air humidity sensor 12, the ozone sensor 13, the drive 7 for the safety flap 6, and the detector for air contaminants 2 are all connected to the control device 18.

The device for air treatment of at least one room 14 operates by air ionization. Downstream of the safety flap 6, the air treatment device 8 is provided to which is connected the supply air channel 10 and the recirculating air channel 15 originating in the room 14. The intake airflow is conveyed by a suction intake device 1 for outside air that is in the form of, for example, an intake air blower, and is connected to the control device 18. The control device 18 controls inter alia the at least one ionization apparatus 9 that is mounted in the supply air channel 10 coming from the air treatment device 8 and extending into the room 14.

As is known in the art, the ionization apparatus 9 is comprised of metal plates with or without openings that are arranged in the form of at least one plate capacitor or at least one cylindrical capacitor. The intake air to be ionized and/or the recirculating air flow through the plates. During corona discharge between the plates the intake air and/or the recirculating air is ionized.

For this purpose, the information in the form of electrical signals derived from

- the first air quality sensor 5 that takes into consideration the quality of the outside air flowing into the air treatment device 8, in particular, the volatile hydrocarbon load—vaporous organic compounds (VOC)—of the outside air or the actual oxidation potential of the outside air,
- the second air quality sensor 17 that is mounted in the recirculating air channel 15 coming from the room 14 and extending to the air treatment device 8 and detects also the volatile oxidizable components of the room air,
- the airflow sensors 4, 11 that measure the flow velocity and thus the amount of conveyed air,
- the air humidity sensor 12, and
- the ozone sensor 13 are evaluated in the control device 18. This is in particular a microcomputer, a computer, or a programmable logic circuit, for example, FPGA.

The second airflow sensor 11, the air moisture sensor 12, and the ozone sensor 13 are mounted in the supply air channel 10 coming from the air treatment device 8 and extending into the room 14.

The second air flow sensor 11 determines the flow velocity in the supply air channel 10 and the air moisture sensor 12 determines the relative air humidity in the supply air channel 10.

In the supply air channel 10 moreover an ozone sensor 13 is mounted that determines the ozone load in the intake air and supplies electrical signals that are equivalent to this load to the control device 18.

The electrical power that is supplied to the ionization apparatus 9 from the control device 18 is adjusted as a function of the values of the first air quality sensor 5, the second airflow sensor 11, the air humidity sensor 12, the ozone sensor 13, and/or the second air quality sensor 17. For this purpose, in the control device 18 the signals from the first air quality sensor 5, the second airflow sensor 11, the air humidity sensor 12, the ozone sensor 13, and the second air quality sensor 17 are linked as data with one another such that the control device 18 provides a situation-appropriate power in the form of alternating pulse rates or several alternating pulse rates combined to packages or sets to the ionization apparatus 9 when a higher amount of air and/or a greater relative air humidity and/or a greater VOC load of the room air occur/s. In these situations, the alternating pulse rate or the number of alternating pulse rates combined to packages is increased. In a positive extreme situation, for example, for no load of the room air, a minimal ionization intensity is still supplied to the ionization apparatus.

For this purpose, in the control device 18 the following occurs:
- weighting of the individual parameters and linking as a sum of the individual vectors,
- a combination as a product of the individual values, or
- any other mathematical treatment, so that the ionization apparatus 9 is operated with a corresponding optimized or desired power.

Figure 2:
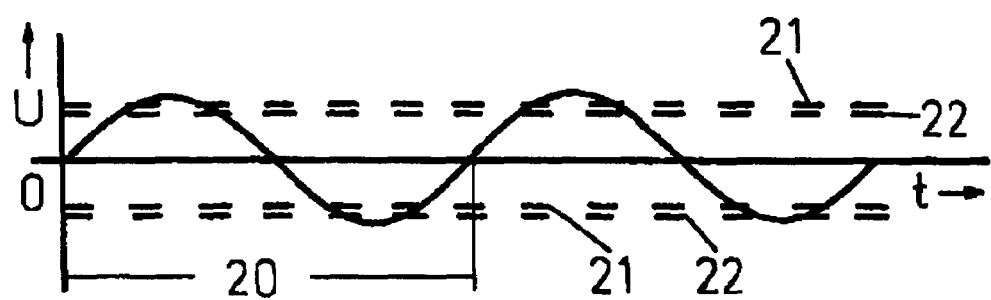
FIG. 2 a basic illustration of a package of two alternating pulses for controlling an ionization apparatus.

The ionization apparatus 9 is operated with temporal sequences of a periodic alternating voltage of identical or approximately identical amplitude. The smallest unit of the sequence is a period of the periodic alternating voltage as an alternating pulse 20 (illustration in FIG. 2). Periods of the periodic alternating voltage that are not required are dismissed. In this way, it is ensured that the voltage during discharge remains constant and the functional data that are important for the entire process are stable as well as controllable. The periodic alternating voltage has a frequency in this connection that corresponds to the mains frequency that is provided, respectively. A frequency converter is not required.

A stable air ionization and thus an optimal efficiency, i.e., a high proportion of positively and negatively charged oxygen ions having a high bonding tendency, for example, with the VOC proportion contained in the air and with a minimal proportion of radicals in the air, is generated only with a defined discharge voltage. It must be maintained constant as much as possible so that a minimal tolerance field is maintained. With the aid of the illustration in FIG. 2, the behavior of the corona discharge upon changing of the discharge voltage when surpassing the limit 21 and dropping below the limit 22 of the tolerance field between the limits 21, 22 of an optimal discharge voltage will be described in the following. When the limit 21 is surpassed upon increasing the voltage of the ionization apparatus 9, the ozone load in the intake air will increase progressively. When the discharge voltage however drops below the limit 22, a working field of air ionization will result that is characterized by a spontaneous corona discharge (buffer effect); this causes the generation of undesirable oxygen radicals or ozone. Accordingly, a defined discharge voltage is maintained constant in the process. A situation-appropriate and stable air ionization is obtained by a corresponding activation of the defined alternating voltage of the sine curve cut at the zero crossing. In this connection, such a sine curve is the alternating pulse 20, respectively, that activates the ionization apparatus 9. For a further optimization of the function of the air ionization the control device 18 is designed such that additionally the alternating pulse rates can be combined to appropriate packages or sets of certain numbers of alternating pulses.

The signal of the ozone sensor 13 are evaluated or used in the process as follows:
- from 0 to 0.06 ppm ozone proportion in the intake air: no action,
- greater/identical to 0.06 ppm ozone proportion: lowering of the momentary ionization power to 50%,
- for a further increase of the ozone proportion, an external ozone source is present, and the measure for decomposing ozone is initiated.

This measure resides in that simultaneously the spacing of the alternating pulses, of the alternating pulse rates and/or the packages of alternating pulses is changed wherein a compensation of the charges of the ionized air occurring in the pauses leads to a conversion of the ozone into natural oxygen clusters/charged oxygen molecules. The energy compensation correspondence substantially to that of nature. Naturally existing oxygen, charged oxygen molecules and ozone in the atmosphere. Ozone is an instable compound that when taking up energy decomposes into charged bipolar oxygen molecules. This process is advantageously used in the pauses in a targeted fashion for ozone decomposition.

The operation of the device for air treatment is moreover carried out such that a minimum ionization power is maintained even when extremely low process data are present. This is particularly the case when the first air quality sensor 5, the second airflow sensor 11, the air humidity sensor 12, the ozone sensor 13, and the second air quality sensor 17 signal to the control device 18 that actually no ionization is needed. In this connection, the adequate natural effect is observed The at least one room is provided directly or indirectly with a recirculaUng channel 15 and has an escape air channel 16, wherein the escape air channel 16 is closable by a driven flap or valve F (flap and valve are only schematically indicated in FIG. 1 by box labeled "F"). A drive member (not illustrated) of the flap or an actuating device of the valve (not illustrated) is connected to the control device 18 for opening or closing the flap or valve.

During operation of the device for air treatment, via the escape air channel 16 only a minimal amount of escape air is discharged, and a corresponding amount of outside air is made available that is supplied via the intake air channel 3.

The control device 18 and/or the drive are provided with at least one manually actuatable switch so that the safety closure is closed after actuation.

In another embodiment, the control device 18 can also be connected to additional sensors or devices that monitor the composition of the room air. In order to increase the duration of airtight closure, several rooms can be connected by channels so that it is also possible to perform air compensation between the rooms.

In a further embodiment, in the intake air channel 3 and/or in the recirculating air channel 15 at least one additional ozone sensor 13a is arranged. This at least one additional ozone sensor 13a is connected to the control device 18 such that it sends an electrical signal in accordance with the level of the ozone contents or an electrical signal in accordance with a predetermined value or several predetermined values of the ozone contents.

In a further embodiment of the safety device for the air in at least one room of a building, the device for air treatment can be connected to a control device and the at least one detector for air contaminants and the drive for the safety closure can be connected to an additional control device.

In further embodiments, other devices for air treatment can be a component of the safety device according to the invention.

What is claimed is:

1. A safety device for the air in at least one room of a building, the safety device comprising:
   at least one intake air channel for supplying outside air to the at least one room;
   at least one exhaust air channel connected to the at least one room;
   at least one device for air treatment comprised of an air treatment device, a first air quality sensor, a second air quality sensor, at least one ionization apparatus, an airflow sensor, an air humidity sensor, and a first ozone sensor;
   a recirculating air channel connecting the at least one exhaustair channel and the air treatment device;
   a supply air channel connecting the air treatment device to the at least one room;
   wherein the first air quality sensor is arranged in the intake air channel or in a supply air channel connected to the air treatment device;

wherein the second air quality sensor is arranged in at least one of the at least one room, the at least one exhaust air channel, and the recirculating air channel;

wherein the at least one ionization apparatus, the airflow sensor, the air humidity sensor and the first ozone sensor are arranged in the supply air channel;

at least one second ozone sensor disposed in at least one of the supply air channel and the recirculating air channel;

at least one detector for air contaminants arranged in the intake air channel, wherein the at least one detector for air contaminants converts at least one input signal into an output signal representing a value of one or several parameters;

at least one control device, wherein the at least one device for air treatment, the at least one detector for air contaminants, and the at least one second ozone sensor are connected to the at least one control device;

a safety flap coupled to a drive, wherein the safety flap is arranged in the air intake channel and wherein the drive is connected to the at least one control device;

wherein the safety flap in an open position opens and in a closed position closes airtightly the intake air channel or an entrance of the at least one device for air treatment, wherein the device for air treatment is arranged in a flow direction of the outside air downstream of the safety flap and wherein, when the at least one detector for air contaminants arranged in the intake channel detects air contaminants, the at least one control device actuates the drive and the drive moves the safety flap from the open position into the closed position to automatically shut off flow of outside air to the at least one device for air treatment and decouple the at least one room from the outside air and cause the exhaust air of the at least one room to be recirculated through the recirculating air channel to the at least one device for air treatment and then through the supply air channel to the at least one room so that a total recirculating operation takes place and the exhaust air is treated again;

wherein, when the safety flap is in the open position, a partial recirculating operation is present through the recirculating air channel to the at least one device for air treatment and then through the supply air channel to the at least one room;

wherein the at least one control device supplies an electrical ionization power to the at least one ionization apparatus which electrical ionization power is adjusted automatically as a function of values of at least one of the first air quality sensor, the airflow sensor, the air humidity sensor, and the second air quality sensor;

wherein, when an ozone level of a certain value is measured by the first and the at least one second ozone sensors, the control device reduces the electrical ionization power;

wherein, when the ozone level increases further or the certain value remains the same, the control device changes a spacing of alternating pulses, of alternating pulse rates and/or of packages of alternating pulses of the electrical ionization power causing conversion of the ozone to natural oxygen clusters (charged oxygen molecules).

2. The safety device according to claim 1, wherein the at least one detector for air contaminants is a sensor for at least one chemical substance, a sensor for at least one biological organism, a dosemeter, or a device for determining air-borne particles.

3. The safety device according to claim 2, wherein the dosemeter is a luminescence dosemeter.

4. The safety device according to claim 1, further comprising an additional airflow sensor arranged in the intake air channel, wherein the additional airflow sensor is connected to the at least one control device.

5. The safety device according to claim 1, wherein the detector for air contaminants is located in an end area of an intake opening of the intake air channel or in an intake device for outside air arranged in the intake air channel.

6. The safety device according to claim 1, wherein a volume of the intake air channel is configured based on at least one parameter selected from the group consisting of an airflow velocity in the intake air channel, a time delay of the detector for air contaminants, a time delay of the control device, and a time delay of the drive including an inertia of the safety flap.

7. The safety device according to claim 1, wherein the drive is a spring return drive.

8. The safety device according to claim 1, wherein the at least one room has an escape air channel, wherein the escape air channel is closable by a driven flap or valve, and wherein a drive member of the flap or an actuating device of the valve is connected to the control device.

9. The safety device according to claim 1, wherein at least one of the control device and the drive is provided with at least one manually actuatable switch such that the safety flap is closed after actuation of the at least one manually actuatable switch.

* * * * *